(12) United States Patent
Robson

(10) Patent No.: US 8,759,287 B2
(45) Date of Patent: Jun. 24, 2014

(54) METHODS OF DECREASING INCISIONAL HERNIA FORMATION AND ACUTE WOUND FAILURE IN OBESE PATIENTS BY ADMINISTERING BASIC FIBROBLAST GROWTH FACTOR

(75) Inventor: Martin C. Robson, Stuart, FL (US)

(73) Assignee: M-3 Biologics, LLC, Fort Worth, TX (US)

( * ) Notice: Subject to any disclaimer, the term of this patent is extended or adjusted under 35 U.S.C. 154(b) by 204 days.

(21) Appl. No.: 13/084,908

(22) Filed: Apr. 12, 2011

(65) Prior Publication Data

US 2012/0264690 A1 Oct. 18, 2012

(51) Int. Cl.
*A61K 38/18* (2006.01)

(52) U.S. Cl.
USPC .......................................................... 514/9.1

(58) Field of Classification Search
None
See application file for complete search history.

(56) References Cited

U.S. PATENT DOCUMENTS

| | | | | |
|---|---|---|---|---|
| 5,725,577 A * | 3/1998 | Saxon | ........................ | 623/23.72 |
| 2001/0006634 A1 * | 7/2001 | Zaleske et al. | ................ | 424/93.7 |
| 2007/0185374 A1 * | 8/2007 | Kick et al. | ........................ | 600/37 |

OTHER PUBLICATIONS

Anthony et al, "Factors affecting recurrence following incisional herniorrhaphy," *World J. Surg.*, 2491: 95-101 (2000).
Brolin et al., "Prospective, Randomized Evaluation of Midline Fascial Closure in Gastric Bariatric Operations," *American Journal of Surgery*, 172(4):328-31 (1996).
DuBay et al., "Progressive fascial wound failure impairs subsequent abdominal wall repairs: a new animal model of incisional hernia formation," *Surgery*, 37(4): 463-71 (2005).
Dubay et al, "The prevention of incisional hernia formation using a delayed-release polymer of basic fibroblast growth factor," *Ann Surg*, 240:179-186 (2004).
Fiddes et al, "Preclinical wound healing studies with recombinant human basic fibroblast growth factor," *Ann NY Acad. Sci.*,368: 316-328 (1991).
Franz, "The biology of hernia formation," *Surg. Clin. North Am.*, 88(1):1-15 (2008).
Franz et al., "Fascial incisions heal faster than skin: a new model of abdominal wall repair," *Surgery*, 129(2): 203-8 (2001).
Grace et al., "Incidence of incisional hernia following dehiscence of the abdominal wound," *Proc. R. Soc. Med.*, 66: 1091 (1973).
Hoer et al, "Influencing factors on the causes of incisional hernia. A retrospective study of 2983 laparotomy patients over a period of 10 years," *Chirurg*, 73(5):474-80 (2002) (Abstract).
Kuhn et al., "Basic Fibroblast Growth Factor in a Carboxymethylcellulose Vehicle Reverses the Bacterial Retardation of Wound Contraction," *Wounds: A Compendium of Clinical Research and Practice*, 13(2):73-80 (2001).
Pollock et al, "Early prediction of late incisional hernias," *Brit J Surg.*, 76: 953-954 (1989).
Robson et al., "Effect of cytokine growth factors on the prevention of acute wound failure," *Wound Rep. Regen.*, 12: 38-43 (2004).
Robson et al., "Sequential Cytokine Therapy for Pressure Ulcers: Clinical and Mechanistic Response," *Annals of Surgery*, 231(4): 600-611 (2000).
Sugarman et al., "Greater risk of incisional hernia with morbidly obese than steroid-dependent patients and low recurrence with prefascial polypropylene mesh," *The American Journal of Surgery*, 171(1): 80-84 (1996).
Wright et al., "The Effect of TGF-β2 in Various Vehicles on Incisional Wound Healing," *Journal of Surgical Investigation*, 2(2):133-143 (2000).
Xing et al, "Impaired laparotomy wound healing in obese rats," *Obesity Surg.*, published online at: www.springerlink.com/content/134xrx2q7284g015 (Feb. 24, 2011).
Metz et al., "Fibrocytes: a unique cell population implicated in wound healing," Cell Mol Life Sci,, 2003, 60(7): p. 1342-50.
Payne et al., "Longterm outcome study of growth factor-treated pressure ulcers," Am. J. Surg. 181: 81-86, 2001.
Robson et al., "The Safety and Effect of Topically Applied Recombinant Basic Fibroblast Growth Factor on the Healing of Chronic Pressure Sores," Annals of Surgery, vol. 216, No. 4, Oct. 1992, pp. 401-408.
Wright et al., "The Effect of TGF-β2 in Various Vehicles on Incisional Wound Healing," I. Journal of Surgical Investigation, 2000, vol. 2, No. 2, pp. 133-143.
Encinosa et al., "Use and costs of bariatric surgery and prescription weight-loss medication," Health Aff. (Millwood), 2005; 24:1039-1046.
DeMaria, E.J., "Bariatric surgery for morbid obesity," New England Journal of Medicine, 356(21):2176-83, May 24, 2007.
Santry et al., "Trends in bariatric surgical procedure," JAMA 294(15):1909-17, Oct. 19, 2005.
Nguyen et al., "Laparoscopic versus open gastric bypass: a randomized study of outcomes, quality of life, and costs," Ann. Surg. 2001; 234:279-291.
Podnos et al., "Complications after laparoscope gastric bypass: a review of 3464 cases," Archives of Surgery, 138(9):957-61, Sep. 2003.
Maclean et al., "Late outcome of isolated gastric bypass," Ann. Surg. 2000, 231;524-528.
Finan et al., "Predictors of wound infection in ventral hernia repair," American Journal of Surgery, 190(5):676-81, 2005.
Weller et al., "Comparing Outcomes of Laparoscopic Versus Open Bariatric Surgery," Annals of Surgery, 24891):10-15, Jul. 2008.

(Continued)

*Primary Examiner* — Robert Landsman
(74) *Attorney, Agent, or Firm* — Barnes & Thornburg LLP; Alice O. Martin

(57) ABSTRACT

Methods for preventing incisional hernia formation and acute wound failure are described. More particularly, methods are described for preventing incisional hernia formation and acute wound failure by administering a composition comprising basic fibroblast growth factor. In addition, a drug delivery device to administer basic fibroblast growth factor is described.

64 Claims, 3 Drawing Sheets

(56) References Cited

OTHER PUBLICATIONS

Hedley et al., "Prevalence of overweight and obesity among US children, adolescents, and adults, 1999-2002," JAMA, 291:2847-2850, 2004.

National Hospital Discharge Survey: Detailed Diagnoses and Procedures, CDC National Center for Health Statistics, 1995.

Thorpe et al., "The impact of obesity on risking medical spending," Health Aff (Millwood), 2004, suppl. web exclusives: w4-480-w4-486.

Burger et al., "Incisional hernia: early complication of abdominal surgery," World J Surg., 2005; 29(12): p. 1608-1613.

Riou et al., "Factors influencing wound dehiscence," Am J Surg., 1992. 163(3): p. 324-30.

Merkow et al., "Effect of body mass indes on short-term outcomes after colectomy for cancer," J Am Col Surg, 2009, 208: p. 53-61.

Keill et al., "Abdominal wound dehiscence," Arch Surg, 1973; 106(4): p. 573.

Baggish et al., "Abdominal wound disruption," Obstet Gynecol, 1975; 46(5): p. 530.

Bucknall, et al., "Burst abdomen and incisional hernia: a prospective study of 1129 major laparotomies," Br Med J (Clin Res Ed), 1982; 284(6320): p. 931-3.

Lamont et al., "Incisional hernia in re-opened abdominal incisions: an overlooked riskfactor," Br J Surg, 1988; 75(4): p. 374-6.

Luijendijk et al., "A comparison of suture repair with mesh repair for incisional hernia," New England Journal of Medicine, 2000; 343(6): p. 392-398.

Burger et al., "Long-term follow-up of a randomized controlled trial of suture versus mesh repair of incisional hernia," Ann.Surg., 2004; 240(4): p. 578-583.

Nascimento et al., "Overweight induced by high-fat diet delays rat cutaneous wound healing," Br J Nut, 2006; 96(6): p. 1069-77.

Biondo-Simoes Mde, L., et al., "Obesity and abdominal wound healing in rats," Acta Cir Bras., 2010, 25(1): p. 86-92.

DuBay et al., "Incisional herniation induces decreased abdominal wall compliance via oblique muscle atrophy and fibrosis," Ann Surg, 2007; 245(1): p. 140-6.

Junqueira et al, "Differential histologic diagnosis of osteoid A Study on human osteosarcoma collagen by the histochemical picrosirius-polarization method," J Pathol, 1986, 148(2) p. 189-96.

Montes et al., "Histochemical and morphological characterization of reticular fibers," Histochemistry, 1980, 65(2): p. 131-41.

Dubay et al., "Fascial fibroblast kinetic activity is increased during abdominal wall repair compared to dermal fibroblasts," Wound Repair Regen, 2004; 12(5): p. 539-45.

Baum et al., "Normal cutaneous wound healing: clinical correlation with cellular and molecular events," Dermatol Surg, 2005; 31(6): p. 674-86; discussion 686.

Sauerland et al., "Obesity is a Risk Factor for Recurrence after Incisional Hernia Repair," Hernia, 2004, 8(1): p. 42-46 (abstract only).

Kurtz et al., "The Zucker fatty rat as a genetic model of obesity and hypertension," Hypertension, 1989; 13(6 Pt 2): p. 896-901.

Strzelczyk et al., "Polypropylene Mesh in Prevention of Postoperative Hernia in Bariatric Surgery,"Ann Surg, 2005; 241(1): 196.

Llaguna et al., "Does Prophylactic Biologic Mesh Placement Protect Against the Development of Incisional Hernia in High-risk Patients?," World J Surg, 2011; 35:1651-1655.

\* cited by examiner

METHODS OF DECREASING INCISIONAL HERNIA FORMATION AND ACUTE WOUND FAILURE IN OBESE PATIENTS BY ADMINISTERING BASIC FIBROBLAST GROWTH FACTOR

BACKGROUND

The number of bariatric surgeries has grown markedly in recent years, increasing more than 400% between 1998 and 2002. In 2010, the number of obese patients undergoing weight loss operations in the US was estimated to be over 200,000. Furthermore, it is projected that approximately one in four bariatric surgeries will be performed using an open laparotomy technique.

The overall major complication rate for open bariatric surgeries is 4% and the overall minor complication rate is 22%. For example, complications of open bariatric surgeries include wound infection and acute wound failure, such as incisional hernia formation. Wound infection is a recognized risk factor for incisional hernia formation. The formation of an incisional hernia results in re-operation of patients almost 100% of the time. Incisional hernia rates have been reported to be 8.9-21% in open bariatric surgeries, and 11% of laparotomy wounds fail and result in the formation of an incisional hernia. The rate of incisional hernia formation is therefore 9-22 times higher in patients undergoing bariatric surgery procedures compared to patients undergoing non-bariatric surgery procedures.

The incidence of wound complication rates is likely related to the obese state of the patients undergoing the bariatric surgery procedures. Previous reports suggest that obese patients have impaired tissue repair compared to non-obese patients. For example, prolonged or increased inflammation in the obese state could contribute to a delay in wound healing due to by a failure to progress to normal fibro-proliferation. Moreover, the obese state could cause an increase in wound failure due to the high mechanical loads placed on the abdominal wall, as well as impaired laparotomy wound healing.

Therefore, a method to prevent acute wound failure and incisional hernia formation associated with bariatric surgeries is disclosed. Methods are described herein for preventing acute wound failure and incisional hernia formation using a composition including basic fibroblast growth factor. Basic fibroblast growth factor is a polypeptide known to exhibit biological activities such as stimulation of cell mitogenesis and chemotaxis.

The methods described herein demonstrate that acute wound failure and incisional hernia formation can be prevented by using a therapeutically effective amount of a composition comprising basic fibroblast growth factor. Through administration during a bariatric surgery, the methods overcome the problems associated with wound complications in an obese patient population following bariatric surgical procedures.

SUMMARY

A method of preventing incisional hernia formation in a patient includes administering to the patient a therapeutically effective amount of a composition comprising basic fibroblast growth factor (bFGF). In addition, a method of preventing acute wound failure in a patient includes administering to the patient a therapeutically effective amount of a composition including bFGF. A therapeutically effective amount gives the desired benefit to the patient and includes both treatment and prophylactic administration. The composition may be administered during a surgical procedure performed or to be performed on the patient. The patient may be obese and the surgical procedure may be a bariatric surgery. The patient may have a body mass index greater than 35.

To administer the composition comprising bFGF, an incision may be made to fascia of a musculofascial layer of the abdominal wall of the patient during the surgical procedure and the composition may be administered at about the time of the incision or at the time of closure of the incision, or both. The composition may be administered into the fascia, into the musculofascial layer, to the edges of the fascia, to the edges of the musculofascial layer, or any combination thereof.

The bFGF may be present in an amount between about 0.1 micrograms and about 10 micrograms per centimeter of the incision, in an amount between about 1 microgram and about 5 micrograms per centimeter of the incision, in an amount of about 5 micrograms per centimeter of the incision, in an amount of about 3 micrograms per centimeter of the incision, or in an amount of about 1 microgram per centimeter of the incision.

The composition may be administered as a single unit dose during a surgical procedure performed or to be performed on the patient.

The composition may further include a carboxymethylcellulose vehicle, a hyaluronic acid vehicle, and/or a fibrin glue vehicle.

A drug delivery device includes a controlled injection syringe, a needle, and bFGF. The device may be adapted to administer the bFGF to a surgical incision of a patient at an amount of between about 1 microgram and about 5 micrograms per centimeter of the incision.

A method of preventing acute wound failure of an abdominal wall includes administering to fascia of the abdominal wall a therapeutically effective amount of a composition comprising bFGF. A therapeutically effective amount is an appropriate amount to give the desired benefit to the incision and includes both treatment and prophylactic administration. The composition may be administered to a location where the incision will be made in the fascia, to the incision in the fascia upon closure of the fascia, or both. The composition may be administered about the time of making the incision in the fascia, at about the time of closure of the fascia, or both. The composition may be administered into the fascia, into the musculofascial layer, to the edges of the fascia, to the edges of the musculofascial layer, or any combination thereof.

The bFGF may be present in an amount between about 0.1 micrograms and about 10 micrograms per centimeter of the incision, or in an amount between about 1 microgram and about 5 micrograms per centimeter of the incision, or in an amount of about 5 micrograms per centimeter of the incision, or in an amount of about 3 micrograms per centimeter of the incision, or in an amount of about 1 microgram per centimeter of the incision.

The composition may be administered as a single dose or as a single unit dose during a surgical procedure performed or to be performed on the patient. The composition may further include a carboxymethylcellulose vehicle, a hyaluronic acid vehicle, and/or a fibrin glue vehicle. The incision may be made on an obese patient during a bariatric surgery procedure. The obese patient may have a body mass index greater than 35.

DETAILED DESCRIPTION

Figure 1:
FIG. 1 shows the abdomen of a patient with a large incisional hernia (arrows) which may be prevented using the methods disclosed herein.

Methods of preventing acute wound failure or incisional hernia in a patient include administering a composition that includes basic fibroblast growth factor (bFGF). Methods of preventing acute wound failure or incisional hernia of an abdominal wall includes applying to fascia of the abdominal wall a therapeutically effective amount of a composition that include bFGF. In addition, a drug delivery device is described to administer the composition.

Methods may utilize administration of a composition for prevention of acute wound failure (alternatively referred to as wound dehiscence, wound disruption, burst abdomen, evisceration, incisional hernia or eventration). As used herein, the term "acute wound failure" refers to the postoperative separation of the abdominal musculoaponeurotic layers, typically recognized within several days and requiring some form of intervention.

Methods may utilize administration of a composition for prevention of an incisional hernia. As used herein, the term "incisional hernia" refers to a defect caused by a prior surgical procedure, for example the protrusion of a portion of an organ or a tissue through an opening.

As used herein, the term "administer" is used in its broadest sense and includes any method of introducing the described composition. According to the invention, a composition containing bFGF may be administered by any conventional route suitable for growth factors, including, but not limited to, parenterally, e.g. injections including, but not limited to, subcutaneously or intravenously or any other form of injections or infusions. Such administration routes and appropriate formulations are generally known to those of skill in the art.

As used herein, the term "patient" refers to a vertebrate, for example an animal. In one embodiment, the animal is a human. In other embodiments, the animal is a non-human animal such as, but not limited to, a non-human primate, horse, cow, goat, pig, rabbit, mouse, guinea pig, dog, or other domestic animal. In another embodiment, the patient is an experimental model or a disease model.

The composition may be administered to a patient who is obese. As used herein, the terms "obese" or "obesity" refer to a condition in which there is an excess of body fat in a patient. Obesity may be due to any cause, whether genetic or environmental. The operational definition of obesity is based on the Body Mass Index (BMI), which is calculated as body weight per height in meters squared ($kg/m^2$). Obesity also refers to a condition whereby an otherwise healthy patient has a BMI greater than or equal to 30.0 $kg/m^2$, or a condition whereby a patient with at least one co-morbidity has a BMI greater than or equal to 27.0 $kg/m^2$. An obese patient is a patient with a Body Mass Index (BMI) greater than or equal to 30.0 $kg/m^2$ or a patient with at least one co-morbidity with a BMI greater than or equal to 27.0 $m^2$. An obese patient may have a BMI of at least about any of 31.0, 32.0, 33.0, 34.0, 35.0, 36.0, 37.0, 38.0, 39.0, and 40.0. For example, the patient's BMI may be greater or equal to 35.0 (i.e., ≥35.0).

The compositions described herein contain basic fibroblast growth factor. As used herein, "basic fibroblast growth factor" (alternatively referred to as "fibroblast growth factor," "basic fibroblast growth factor-2," or "bFGF") is either naturally-occurring or produced recombinantly. The sequence of bFGF is known in the art, including, for example, the sequence displayed in U.S. Pat. No. 5,136,025. bFGF has biological activity as shown in any assay known to those of skill in the art. As used herein, bFGF also includes analog proteins and fragments of the full length bFGF sequence that have similar biological activity but may contain accidentally or deliberately induced alterations such as deletions, additions, extensions or exchanges of amino acid residues.

The amount of bFGF present in the composition is adequate to achieve a therapeutic effect. As used herein, the term "therapeutically effective amount" refers to an amount which gives the desired benefit to an animal and includes both treatment and prophylactic administration. The amount is not expected to vary from one individual to another and depends primarily on the length of the fascia incision which may be related to the underlying cause of the condition to be treated. A therapeutically effective amount of the present compositions may be readily ascertained by one of ordinary skill in the art using available materials and procedures.

The compositions may also optionally include one or more other active ingredients, in addition to bFGF. As used herein, the term "active ingredient" or "therapeutic ingredient" refers to a therapeutically active compound, as well as any prodrugs thereof and pharmaceutically acceptable salts, hydrates and solvates of the compound and the prodrugs. Other active ingredients may be combined with bFGF and may be either administered separately or in the same pharmaceutical formulation. The amount of other active ingredients to be given may be readily determined by one skilled in the art based upon therapy with bFGF.

The prevention of acute wound failure or of an incisional hernia may be associated with a surgical procedure performed or to be performed on the patient. Methods and compositions described herein are suitable for a surgical procedure termed bariatric surgery. As used herein, the term "bariatric surgery" refers to any surgical procedure that is performed to facilitate weight loss in a patient.

During the surgical procedure, an incision may be made to an abdominal wall fascia. As used herein, the term "incision" refers to any surgical penetration and includes, by way of example, incisions made by needles, knives (including surgical knives and surgical cautery knives), trocars, and the like. As used herein, the term "abdominal wall" refers to the lining of the abdomen, including the layers present between the skin and the abdominal cavity of a patient. The abdominal wall includes, for example, the posterior, lateral, and anterior walls. As used herein, the term "fascia" refers to a band of tissue below the skin that covers the underlying tissues and/or separates the different layers of tissue. Fascia includes multiple layers, including but not limited to superficial fascia, deep fascia, musculofasica, and subserous fascia.

The composition described herein may be administered to a location where the incision will be made in the abdominal wall fascia or in the abdominal wall musculofascial layer. In one embodiment according to the described methods, the composition is administered at about the time of making the incision. In another embodiment according to the described methods, the composition is administered at about the time of closure of the incision. In yet another embodiment according to the described methods, the composition is administered to a location where the incision will be made and during the closure of the incision.

The composition described herein may be administered into the fascia, into the musculofascial layer, or both. In addition, during closure, the composition may be administered to the edges of the fascia, into the musculofascial layer, or both. As used herein, the term "edge" refers to the edge of the fascia or the musculofascial layer that is created upon an incision.

According to the disclosed methods, the composition may be administered wherein the bFGF is present in an amount between about 0.1 microgram and about 10 micrograms per centimeter of the incision. In another embodiment, the composition is administered wherein the bFGF is present in an amount between about 1 microgram and about 5 micrograms per centimeter of the incision. In yet another embodiment, the composition is administered wherein the bFGF is present in an amount of about 5 micrograms per centimeter of the incision. In yet another embodiment, the composition is administered wherein the bFGF is present in an amount of about 3 micrograms per centimeter of the incision. In yet another embodiment, the composition is administered wherein the bFGF is present in an amount of about 1 microgram per centimeter of the incision.

As used herein, the term "unit dose" is a discrete amount of the composition comprising a predetermined amount of bFGF. The amount of bFGF is generally equal to the dosage of bFGF which would be administered to a patient or a convenient fraction of such a dosage such as, for example, one-half or one-third of such a dosage.

As used herein, the term "single unit dose" in ug/cm of the composition can be administered to a patient in a single application at one location on the patient.

The composition may also further include a vehicle. As used herein, the term "vehicle" refers to any composition that is suitable for use as a diluent, solvent, or other composition suitable for producing a suspension. In one embodiment, the vehicle is a carboxymethylcellulose vehicle. In another embodiment, the vehicle is a hyaluronic acid vehicle. In yet another embodiment, the vehicle is a fibrin glue vehicle.

In addition to preventing acute wound failure or incisional hernia formation, administration of a composition including bFGF can accelerate the rate of gain of strength of an incision post-operatively. Accordingly, this may allow for a patient to regain normal activities more quickly following a surgical procedure.

Furthermore, the methods described herein may be performed at the time of re-operation in order to prevent a recurrence of acute wound failure or incisional hernia formation.

Wound failure can be evaluated, for example, using a metal clip evaluation to determine the presence or absence of acute wound failure. In one embodiment, radio-opaque, metal surgical clips may serve as markers of wound failure and x-ray images may be use to determine the incidence Examples are provided for illustrative purposes and are not intended to limit the scope of the disclosure.

EXAMPLE 1

Wound Failure Study of a bFGF Composition Administered to Obese Animals

A study of the described methods can be undertaken to compare incidence of wound failure in obese animals following administration of a composition including bFGF.

Genetically obese Zucker rats, aged 9 weeks and weighing approximately 400 grams, can be acclimated and housed under standard conditions and can be provided ad libitum food and water throughout the study. Two experimental models can be used simultaneously for the obese rats: a rat laparotomy wound healing model and an incisional hernia model.

A: Laparotomy wound healing model—A 6×3 centimeter (cm) ventral full-thickness skin flap can be raised through the avascular prefascial plane, and a 5 cm full-thickness laparotomy incision can be made through the linea alba of the musculo-fascial layer of the abdominal wall. The laparotomy can then be repaired in a standardized manner with a continuous running 4-0 polypropylene suture using 0.3 cm suture bites and 0.5 cm progress between stitches. The skin flap can be returned and sutured into place with 4-0 polypropylene suture and steel wound clips.

On post-operative day (POD) 14, the rats can be sacrificed and the abdominal walls can be excised. The skin layer can be removed. Isolated abdominal wall (laparotomy wound, muscle, and fascia) strips can then be designed for biomechanical testing. Mechanical testing can be performed on the abdominal wall strips as known in the art. All sutures can be removed. Abdominal wall strips can be taken perpendicular to the wound healing interface. A cutting template can be used to measure the abdominal wall and minimize size variability between specimens. Strips can be cut 10 millimeters (mm) in width and 60-80 mm in length. Two strips can be collected from each rat and testing can be performed within 6 hours of necropsy. To standardize tensile strength measurements, the abdominal wall tissue strip thickness at the laparotomy wound and the length between load grips can be measured with Digimatic calipers. Stretch loading can facilitate mechanical characterization of the wound healing interface. Force extension curves can be generated for each abdominal wall strip with the use of an Instron tensiometer equipped with a 50 Newton static load cell set at a crosshead speed of 10 mm per minute. The load frame applies testing can load to the abdominal wall strips until mechanical tissue disruption occurs. The anatomic location of the break can be noted for each specimen. Force and tissue deformation can be simultaneously recorded. Data analysis can be performed with the use of the Merlin material testing software package from which breaking strength, the maximum load force at mechanical failure, tensile strength, the maximum stress developed in the specimen per unit area, energy at break, yield strength, yield energy, and stiffness can be generated. The strength of the specimen can be defined at the yield point where the laparotomy wound is irreversibly deformed beyond the elastic limit. This parameter can indicate laparotomy wound failure.

B: Incisional hernia model—Again, a 6×3 cm ventral full-thickness skin flap can be raised through the avascular prefascial plane, and a 5-cm full-thickness laparotomy can be made through the linea alba. In this model, two fast absorbing 5-0 plain catgut sutures can be used to close the laparotomy wound. This model can result in intentional acute mechanical failure of the laparotomy wound and progression to incisional hernias. The flap can be returned and sutured in place with 4-0 polypropylene stitches and steel wound clips.

The hernia model rats can be euthanized on POD 28. The skin can be dissected free circumferentially and a 5 cm×10 cm section of the abdominal wall can be excised. The specimen can be stretched out and pinned down on a dissecting board at the four corners with the peritoneal side up. A ruler can be set alongside the wound as a reference for every sample. A standardized image can then be captured using a digital camera. Software Spot (Windows: Version 4.5) can be used to calculate the hernia size based on the digital image. Calibration can be established using the ruler for reference for each image. An outline can be drawn along the hernia ring and the hernia size can be calculated in square centimeters.

Animal treatment groups—A total of 43 genetically obese Zucker rats can be used according to these procedures. For example, eight rats can be used in the laparotomy wound healing model and 35 rats can be used in the incisional hernia model. The 43 rats can be divided into seven treatment groups as follows: Group 1: control animals administered 0.9% NaCl (n=7); Group 2: animals administered bFGF in 0.9% NaCl (n=7); Group 3: animals administered bFGF in 0.9% NaCl @ 2.5 ug/cm (n=7); Group 4: animals administered bFGF in 0.9% NaCl @ 5 ug/cm (n=7); Group 5: animals administered bFGF in carboxymethylcellulose @ 5 ug/cm (n=5); Group 6: animals administered bFGF in dilute hyaluronic acid @ 5 ug/cm (n=5); and Group 7: animals administered bFGF in dilute fibrin glue @ 5 ug/cm (n=5).

In each group of animals, the test substance (i.e., control or bFGF solution) can be injected into the planned line of fascial incision immediately prior to incising the abdominal wall fascia. Moreover, the test substance can be injected into the two opposing edges of the musculofascial layer of the abdominal wall at the time of closure of that layer of the wound. Two animals in Groups 1-4 can be sacrificed at 14 days for wound strength testing in model A: the rat laparotomy wound healing model. The remaining five animals in groups 1-4 and all five animals in groups 5-7 can be sacrificed on POD 28 for incisional hernia evaluation in model B: the incisional hernia model. This experiment may be used to evaluate the optimal dose of bFGF per cm of fascia incision in humans, as well as potential vehicles for delivery of bFGF.

EXAMPLE 2

Wound Healing Study in an Obese Rat Model

The study was undertaken to evaluate if obesity in rats caused an increase in laparotomy wound failure due to the high mechanical loads placed across the abdominal wall. One goal was to establish the time-course for early laparotomy wound healing and the recovery of mechanical wound strength in the setting of obesity. Another goal was to quantify the expected increase in laparotomy wound failure and incisional hernia formation in the obese rats and to correlate the findings with fibroblast function and collagen synthesis.

Materials: Low glucose Dulbecco's modified Eagle's medium (DMEM) and penicillin/streptomydn antibiotics were purchased from Invitrogen (Carlsbad, Calif.). Fetal bovine serum (FBS) was purchased from Hyclone Laboratories, Inc. (Logan, Utah). Saturated aqueous solution of picric acid and Sirius red F3B (C.I. 35782) were purchased from Sigma-Adrich Corp. (St. Louis, Mo.). Cell Counting Kit-8 (CCK-8) was purchased from Dojindo Molecular Technologies, Inc. (Gaithersburg, Md.).

Laprotomy Wound Healing Model: Sprague-Dawley (SD) rats (Charles River, Wilmington, Mass.), age 9 weeks and weighing 250 g, and genetically obese Zucker rats (Charles River, Wilmington, Mass.), aged 9 weeks and weighing 400 g, were acclimated and housed under standard conditions. Animals were provided ad libitum intake of standard rat chow and water throughout the study.

Briefly, a 6×3 cm ventral full-thickness skin flap is raised through the avascular prefascial plane, and a 5-cm full-thickness laparotomy incision is made through the linea alba of the musculo-tendinous layer of the abdominal wall. The laparotomy is then repaired in a standardized manner with a continuous running 4-0 polypropylene suture using 0.3 cm suture bites and 0.5 cm progress between stitches. The suture is tied to itself at the caudal end of the wound. The skin flap is returned and sutured in place with 4-0 polypropylene sutures and steel wound dips. After 30 minutes of recovery under a heat lamp, the rats are returned to fresh individual cages.

Two groups were studied: 1) normal weight SD rats and 2) obese Zucker rats. On postoperative day (POD) 7, 14, 21 and 28, the rats were sacrificed and the abdominal walls were excised. The skin layer was removed. Isolated abdominal wall (laparotomy wound, muscle and tendon) strips were then designed for biomechanical testing. Fresh biopsies of the abdominal wall—laparotomy wound interface were also collected for histological staining.

Laparotomy Wound Strength and Bio-Mechanical Properties: Mechanical testing was performed on standardized abdominal wall strips collected from the laparotomy wound healing model. All sutures were removed. Abdominal wall strips were taken perpendicular to the wound healing interface. A cutting template was used to measure the abdominal wall and minimize size variability between specimens. Strips were cut 10 mm in width and 60-80 mm in length. Two strips were collected from each rat and testing was performed within 6 hours of necropsy. To standardize tensile measurements, the abdominal wall tissue strip thickness at the laparotomy wound and the length between load grips were measured with Digimatic calipers (Mitutoyo American Corp, Chicago, Ill.). Stretch loading facilitated mechanical characterization of the wound-healing interface. Force extension curves were generated for each abdominal wall strip with the use of an Instron tensiometer (model 5542; Instron Corporation, Canton, Mass.) equipped with a 50 Newton static load cell set at a crosshead speed of 10 mm per minute. The abdominal wall strips were mounted into the load frame with the use of pneumatic grips preloaded to 0.1 Newtons with the gauge length measured between the grips set to approximately 10 mm. The load frame applied testing loads to the abdominal wall strips until mechanical tissue disruption occurred. The anatomic location of the break was noted for each specimen. Force and tissue deformation data were simultaneously recorded and captured on a computer connected to the load frame via a digital interface card. Data analysis was performed with the use of the Merlin materials testing software package (Instron Corp, Canton, Mass.) from which breaking strength, the maximum load force ($F_{max}$) at mechanical failure (N); tensile strength, the maximum stress developed in the specimen per unit area, calculated as $F_{max}$/cross-sectional area (N/mm$^2$); energy at break (mJ); yield strength (N); yield energy(mJ); and stiffness, the slope of the linear elastic region of the force-extension curve (N/mm), were generated with the Merlin software package. The strength of the specimen was defined at the yield point where the laparotomy wound irreversibly deformed (beyond the elastic limit) indicating laparotomy wound failure.

Incisional Hernia Model: A 6×3 cm ventral full-thickness skin flap was again raised through the avascular prefascial plane, and a 5 cm full-thickness laparotomy incision was made through the linea alba. In the hernia model, two fast absorbing 5-0 plain catgut sutures were used to close the laparotomy wound. This model results in intentional mechanical failure of the laparotomy wound and progression to incisional hernias. The skin flap is returned and sutured in place with three 4-0 polypropylene stitches and steel wound clips.

Hernia Size: The hernia model rats were euthanized on POD 28. The skin was dissected free circumferentially and a 5 cm×10 cm section of the abdominal wall was excised. The specimen was stretched out and pinned down on a dissecting board at the four corners with the peritoneal side up. A ruler was set alongside the wound as a reference for every sample. A standardized image was then captured using a digital camera. Software Spot, Windows: Version 4.5 (Diagnostic Instruments, Inc. University of New South Wales) was used to calculate the hernia size based on the digital image. Calibration was established using the ruler for reference on each image. An outline was drawn along the hernia ring and the hernia size calculated in square centimeters.

Laparotomy Wound and Abdominal Wall Histology: Sagittal abdominal wall and laparotomy wound and/or hernia sections were then cut and immediately fixed in 10% neutral-buffered formalin in preparation for histologic analysis. Specimens were embedded in paraffin, sectioned, and stained with hematoxylin and eosin or trichrome by the Immunoperoxidase Laboratory at the University of Michigan Comprehensive Cancer Center to confirm the quality of the samples.

Collagen Isoform Synthesis: Picrosirius red staining for collagen was performed as reported by Puchtler et al with minor modifications. Paraffin sections were de-waxed and hydrated on glass slides. Nuclei were stained with Weigert's haematoxylin for 8 minutes, and then the slides were washed for 10 minutes in running tap water. They were then stained in picrosirius red for one hour followed by washing in two changes of acidified water. Most of the water was removed from the slides by vigorous shaking. They were then dehydrated in three changes of 100% ethanol, cleared by immersion in xylene and mounted in a resinous medium.

Microscopy and Image Capture: To visualize the bi-refringent collagen, an Olympus BX-51 upright light microscope with an Olympus DP-70 high resolution digital camera (Olympus Corporation Japan) was employed to obtain digital images. The stained collagen fibers displayed as bright, green to red color based on collagen isoform subtype. All slides were photographed on the same day to avoid any variability associated with the light source.

Rat Abdominal Wall Musculo-tendon Fibroblast Cell Culture: Biopsies of unwounded linea albas of SD and Zucker rats were treated in 0.0125% trypsin at 37° C. for 30 min. The peritoneal side of the biopsies was scraped to remove mesothelial cells. Biopsies were minced in culture medium, spread on the bottom of T-75 $cm^2$ flasks and allowed to stand undisturbed for two hours at 37° C. in 5% $CO_2$ until the pieces adhered to the flask bottom. Medium was then gently drained. DMEM culture media containing 15% FBS and 1,000 p/ml penicillin G, and 1,000 pg/ml streptomycin sulfate solution was then slowly added to the culture flask, and the tissue samples were incubated at 37° C. in 5% $CO_2$. The medium was changed every two days, and the abdominal wall fibroblast primary cell cultures were grown to confluence for passage. Experimental fibroblasts were used at passages two to four. The same source fibroblasts grown to confluence were harvested for fibroblast-populated collagen.

Fibroblast-populated Collagen Lattices (FPCL): Trypsinized abdominal wall fibroblasts were suspended in cold DMEM. Six-well tissue culture plates were precoated with 4% BSA in PBS for 24 h. For FPCL with fibroblasts cultured on the surface of the collagen gels (FPCL-S), DMEM 1.3 ml plus FBS 0.2 ml plus type I collagen stock solution 0.5 ml were mixed to yield a final concentration of 1.25 mg/ml of collagen. This collagen working solution (2 ml) was added to each well. After polymerization at 37° C., 105 fibroblasts were poured on each collagen gel in 2 ml; DMEM containing 10% FBS. The plates were incubated in a cell culture incubator for 3 h until cells adhered to the gel surface. The gels were then detached from the well sidewalls by gently scoring around the circumference with a fine pipette tip.

For the mixed fibroblast collagen gels (FPCL-M), 105 fibroblasts in 1.3 ml DMEM suspension plus FBS 0.2 ml plus type I collagen stock solution 0.5 ml were mixed to yield a final concentration of 1.25 mg/ml of collagen. This collagen mixture (2 ml) with three-dimensionally embedded fibroblasts was then added to each well. Gel polymerization progressed at 37° C. for 3 h before being circumferentially detached. After polymerization at 37° C., 2 mL DMEM containing 10% FBS was added to each well. After detachment, gel diameter was measured with a ruler and the gel area was calculated at designated time points.

Cell Proliferation Assay: Cell proliferation was determined by a cell viability assay. Cell viability was detected using CCK-8. Abdominal wall fibroblasts were seeded 3000 cells/well in a 96-well plate. At designed time points, culture medium was replaced with 100 pl fresh FBS free DMEM containing 1,000 pg/mI penicillin G, and 1,000 pg/ml streptomycin sulfate plus 10 pl CCK-8. The plates were then incubated at 37° C. for 1 hour and O.D. values were read at 450 nm with 690 nm as a reference wave length to determine the cell viability in each well. Fibroblasts from each group were used to generate cell number-cell viability standard curves for calibration.

Figure 2:
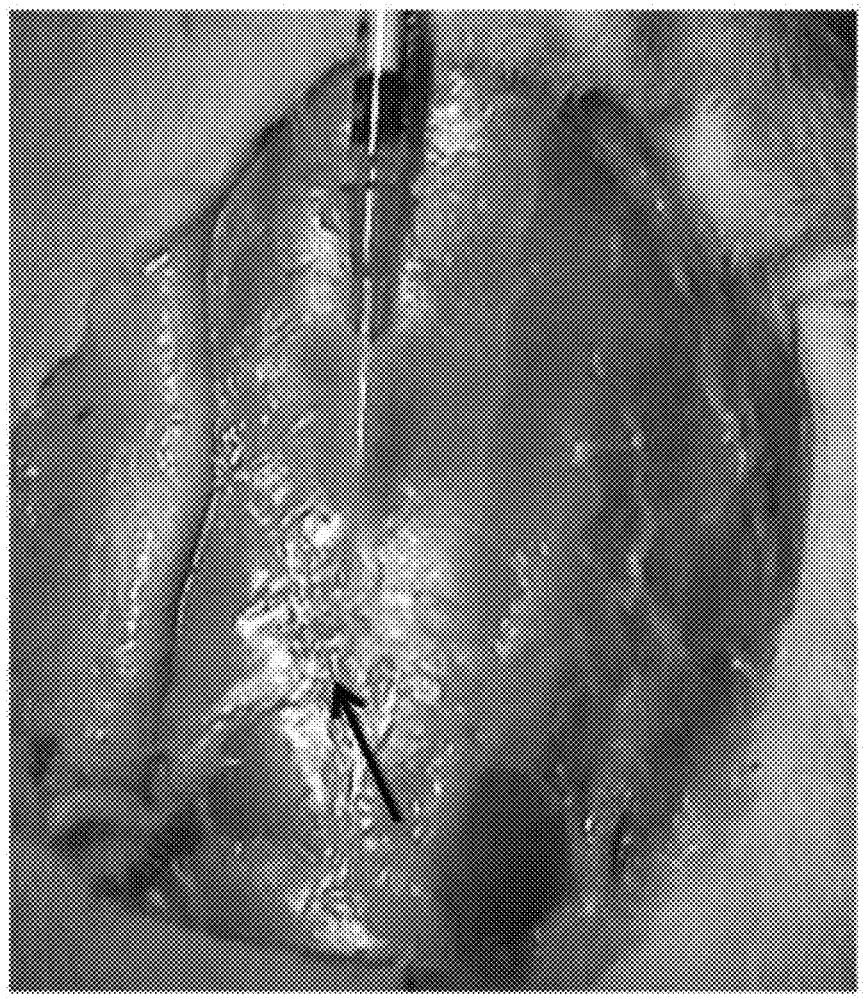
FIG. 2 shows administration of the described composition into fascia of rat abdominal wall (arrow) prior to incision into the fascia of the musculofascial layer.
Figure 3:
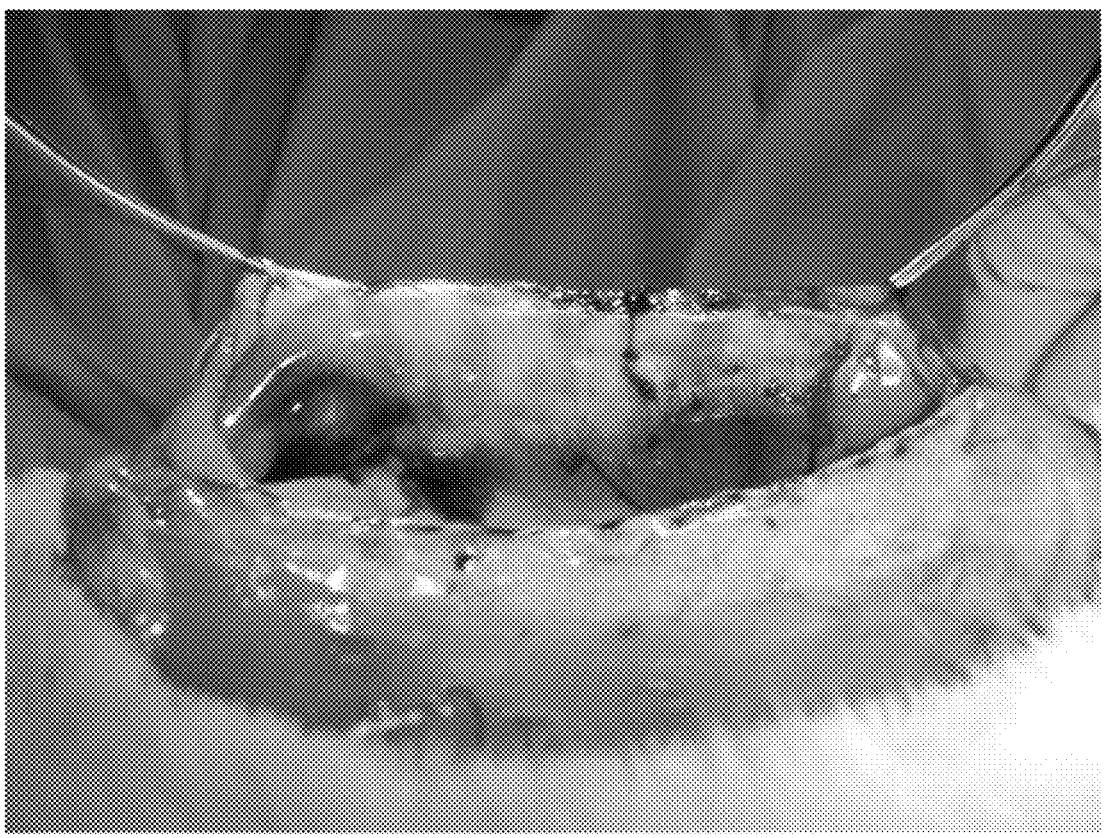
FIG. 3 shows the musculofascial layer of the abdominal wall of FIG. 2 after incision. Methylene blue dye was injected to demonstrate dispersion within the musculofascial layer. The edges of the musculofascial layer of the abdominal wall are also visible.

Mechanical Properties of the Healing Laparotomy Wounds: Tensiometric analysis was performed on uniform abdominal wall strips with the line of tissue deformation directly perpendicular to the linea alba and laparotomy incision. The laparotomy wounds of the normal weight SD rats were stronger than those of the obese Zucker rats at all time points. Wound disruption always occurred at the abdominal wall-laparotomy wound interface. As shown in FIG. 2, the breaking strength of laparotomy wounds in SD rats was significantly higher than that of Zucker rats by POD 14 and through POD 28. The differences in tensile strength suggest a significant mechanical defect in the wound healing matrix of the obese Zucker rat, despite its greater size. The lagging energy at break (energy absorbed), stiffness, yield load and yield energy together suggests a weaker laparotomy wound in the obese rats.

Collagen Ill is the weaker isoform of collagen typically secreted into an early, provisional wound matrix. As wound maturation occurs, increased levels of the stronger collagen I appear, resulting in the normal increase in wound strength. Histological samples were taken of the healing laparotomy wounds between the rectus muscles. Thicker collagen type I fibers stain red-orange with cross-polarization microscopy, and thinner collagen type III fibers stain green. At POD 7, the early laparotomy wound tissue was loose and stained predominantly for the provisional collagen type III isoform (green). By POD 14, the collagen type III content and wound tissue density in Zucker rat wounds remained similar to that of POD 7 (delayed maturation). A normal pattern of collage type III decrease was observed in the SD rat wounds by POD 14, and collagen I based wound density increased significantly as the collagen fiber structure became more organized. Together these findings indicate delayed laparotomy wound maturation and remodeling in obese Zucker rats, consistent with the observed weaker mechanical strength of the wounds.

To quantify the consequences of laparotomy dehiscence in obese versus normal weight rats, the rat incisional hernia model was used. On POD 28, all rats were euthanized and the abdominal walls were excised to measure the extent of laparotomy wound failure. The wound defect size in the obese Zucker group was significantly larger than those in the normal weight SD rat group, $12.06 \pm 0.62$ $cm^2$ versus $4.2210.43$ $cm^2$.

Rats in both groups significantly gained body weight over the 28-day postoperative period, indicating no nutritional or intestinal differences.

In a human study of incisional hernia formation, it was found that a 12 mm gap in the laparotomy closure on POD 30 would go on to form a clinically significant incisional hernia 94% of the time. Conversely, defects less than 12 mm in size formed clinically significant incisional hernias less than 1% of the time over three years. Within limits, small laparotomy defects during the early postoperative period do not tend to form incisional hernias, but larger ones do. The majority of SD rats developed relatively small laparotomy defects, if at all. The largest and smallest hernia or defect sizes were 6.28 $cm^2$ and 0.50 $cm^2$ in SD rat group versus 16.12 $cm^2$ and 8.30 $cm^2$ in the obese Zucker rat group, respectively.

Normal fibroblast function is required for effective wound repair. To determine whether fibroblast function is impaired in obese Zucker rats, the intrinsic kinetic activity of fibroblasts derived from the un-wounded linea alba of SD and Zucker rats was measured, by FPCL for binding to and remodeling a collagen matrix in vitro. Collagen lattice compaction was compared in two matrix models, FPCL-S and FPCL-M. The majority of the fibroblast collagen lattice compaction occurred in the first 24 hours in the FPLC-S model, whereas FPCL-M contraction progressed more slowly. Decreased fibroblast kinetic activity was pronounced in fibroblasts derived from obese rats in both FPCL models. Fibroblasts derived from Zucker and SD rats achieved 52.36±3.93% and 36.18±5.13% compaction at 24 hours in FPCL-M, and 42.94±1.90% and 27.16±2.24% compaction at 2 hours in FPCL-S, respectively. Fibroblasts cultured from Zucker rat linea alba were significantly less efficient in causing lattice compaction and achieved less overall lattice compaction when compared to SD fibroblasts. To determine if the difference in fibroblast collagen matrix compaction between SD and Zucker rats was due to differences in fibroblast number, cell proliferation assays were performed to generate a time-course and FBS dose-response curves for normal and obese rat fibroblasts. Metabolic proliferation assays revealed no significant differences in proliferation between obese versus normal weight fibroblasts in either an FBS concentration or time dependent manner.

The high incidence of laparotomy wound failure leading to incisional hernias in obese subjects may be due to impaired laparotomy wound healing. It is clinically assumed that the problem of laparotomy wound failure and incisional hernia in obese patients is due primarily to increased mechanical loading across the obese abdominal wall. Many surgeons even advocate all forms of weight loss prior to considering laparotomy or incisional hernia repair. The results presented here suggest that the high incidence of laparotomy wound failure in obesity is also due to impaired laparotomy wound healing, exacerbating the mechanical disadvantage.

The mechanical strength of an early surgical wound is normally established by a sequential series of coordinated molecular and cellular processes, including inflammatory and repair cell proliferation and the deposition of a provisional extracellular matrix. After an initial inflammatory lag-phase where there is minimal mechanical strength in the wound, the proliferative phase of wound healing predominates, approximately four days following tissue injury. Fibroblasts, the most important cellular components during this repair phase, reach their peak biological activity approximately within 14-21 days of wounding. Normally, a provisional or early wound matrix is established to support repair cell ingrowth. This early wound matrix is mechanically weaker than a mature acute wound matrix, expressing higher levels of the thin fibril collagen isoform, collagen type III. In this study, there was higher immature collagen III content in the laparotomy wounds of the obese rats in the early postoperative period. In a skin wound model, it was observed that mice predisposed to obesity, but maintained at normal weight by dietary restriction exhibited normal collagen accumulation, but deficient wound collagen formation and accumulation was seen when allowed to develop obesity. This defect was not reversible and could not subsequently be corrected by insulin treatment and dietary restriction. The same animals when chronologically mature expressed normal wound collagen accumulation if they had never been obese. Other studies also suggest a biological defect in wound healing exists in the setting of obesity. It has been reported that retarded skin wound contraction and deficient wound collagen formation was observed in obese C57-BL ob/ob mice compared with lean mice. In calorie diet induced obese Wistar rats, it has been observed that obesity lowered the mechanical strength of the aponeurotic scars but not the skin scars, supporting important differences in the wound healing mechanisms of abdominal wall fascia and skin. In this study of aponeurotic wound healing, obesity did not appear to induce a delayed inflammatory response or impaired collagen density. In wound healing models of tympanic membrane perforation, the Zucker diabetic fatty rats demonstrated a significantly prolonged time to closure compared with normal weight Sprague-Dawley rats. The obese Zucker rat model shares some of the clinical signs of obesity in humans. For example, these animals are glucose intolerant slightly hypertensive and pass protein in their urine. They have kidney dysfunction even though they are not yet diabetic. It is possible that any or all of these markers for the metabolic disturbance contribute to abdominal wall repair fibroblast dysfunction through systemic signaling or inhibition.

Connective tissue fibroblasts are the most important cell type responsible for the tissue remodeling and wound strength. Fibroblasts synthesize extracellular matrix, can signal angiogenesis and promote tissue remodeling. In obese mice, contraction of an open skin wound is significantly delayed. In the current study, laparotomy wound closure was significantly impaired in obese rats compared with normal weight rats. Delayed wound contraction suggests a defect in repair fibroblast function. Repair fibroblasts cultured from obese rats were defective in the ability to cause collagen matrix contraction, a measure of wound organization. There was no measurable defect in fibroblast proliferation.

Obese rats express impaired laparotomy wound healing, most importantly measured as a significant delay in the recovery of wound mechanical strength. A potential cellular defect is identified within fibroblasts isolated from the obese rat.

Publications

These publications are incorporated by reference to the extent they relate materials and methods disclosed herein.

1 Robson et al., "Clinical Studies on Growth Factors in Pressure Sores: Preliminary Report, Clinical and Experimental Approaches to Dermal and Epidermal Repair: Normal and Chronic Wounds, pp. 95-102 (1991)

2 Robson et al., "Effect of cytokine growth factors on the prevention of acute wound failure," Wound Repair and Regeneration, Vol. 12, No. 1, January-February 2004, pp. 38-43

3 Kuhn et al., "Basic Fibroblast Growth Factor in a Carboxymethylcellulose Vehicle Reverses the Bacterial Retardation of Wound Contraction," Wounds: A Compendium of Clinical Research and Practice, Vol. 13, No. 2, march/April 2001, pp. 73-80

4 Fiddes et al., "Preclinical Wound-Healing Studies with Recombinant Human Basic Fibroblast Growth Factor," Annals New York Academy of Sciences, pp. 316-328

5 Robson et al., "Sequential Cytokine Therapy for Pressure Ulcers: Clinical and Mechanistic Response," Annals of Surgery, Vol. 231, No. 4, April 2000, pp. 600-611

6 Phillips, et al., "Correction of diabetic incisional healing impairment with basic fibroblast growth factor," Surg. forum 41: 602-603, 1990

7 Stenberg et al., "Effect of bFGF on the inhibition of contraction caused by bacteria," J. Surg. Res. 50: 47-50, 1991

8 Robson et al., "Clinical studies on growth factors in pressure sores," Prog. Clin. Biol. Res. 365:95-102, 1991

9 Hayward et al., "Local infiltration of an angiogenic growth factor does not stimulate the delay phenomenon," Brit. J. Plast. Surg. 44: 526-529, 1991

10 Fiddes et al., "Preclinical wound healing studies with recombinant human basic fibroblast growth factor," Ann. NY Acad. Sci. 368: 316-328, 1991

11 Hayward et al., "Fibroblast growth factor reverses the bacterial retardation of wound contraction," Am. J. Surg. 163: 288-293, 1992

12 Robson et al., "The safety and effect of topically applied recombinant basic fibroblast growth factor on the healing of chronic pressure sores," Ann. Surg. 216: 288-292, 1992

13 MacCauley et al., "Cytoprotection of human dermal fibroblasts against silver Sulfadiazine using recombinant growth factors," J. Surg. Res. 56; 378-384, 1994

14 Smith et al., "Efficacy of growth factors to accelerate closure of interstices in explanted human meshed grafts," J. Bur Care & Rehab. 21:5-9, 2000

15 Robson et al., "Sequential cytokine therapy for pressure ulcers: Clinical and mechanistic response," Ann. Surg. 231:600-611, 2000

16 Payne et al., "Longterm outcome study of growth factor-treated pressure ulcers," Am. J. Surg. 181: 81-86, 2001

17 Kuhn et al., "Basic fibroblast growth factor in a carboxymethyl cellulose vehicle reverses the bacterial retardation of wound contraction," Wounds 13: 73-80, 2001

18 Dubay et al, "The prevention of incisional hernia formation using a delayed-release polymer of basic fibroblasts growth factor," Ann. Surg. 240: 179-186, 2004

19 Robson et al., "Effect of cytokine growth factors on the prevention of acute wound failure," Wound Rep. Regen. 12: 38-43, 2004

20 Robson et al., "The Safety and Effect of Topically Applied Recombinant Basic Fibroblast Growth Factor on the Healing of Chronic Pressure Sores," Annals of Surgery, Vol. 216, No. 4, October 1992 pp. 401-408

21 Wright et al., "The Effect of TGF-β32 in Various Vehicles on Incisional Wound Healing," I. Journal of Surgical Investigation, Vol. 2, No. 2, pp. 133-143

22 Encinosa et al., "Use and costs of bariatric surgery and prescription weight-loss medication," Health Aff. (Millwood), 2005; 24:1039-1046

23 DeMaria, E. J., "Bariatric surgery for morbid obesity," New England Journal of Medicine, 356(21):2176-83, May 24, 2007

24 Santry et al., "Trends in bariatric surgical procedure," JAMA 294(15):1909-17, Oct. 19, 2005

25 Nguyen et al., "Laparoscopic versus open gastric bypass: a randomized study of outcomes, quality of life, and costs," Ann. Surg. 2001; 234:279-291

26 Podnos et al., "Complications after laparoscope gastric bypass: a review of 3464 cases," Archives of Surgery, 138 (9):957-61, September 2003

27 Maclean et al., "Late outcome of isolated gastric bypass," Ann. Surg. 2000, 231; 524-528

28 Finan et al., "Predictors of wound infection in ventral hernia repair," American Journal of Surgery, 190(5):676-81, 2005

29 Pollock et al., "Early prediction of late incisional hernias," Brit. J. Surg. 76:953-4, 1989

30 Brolin et al., "Prospective, Randomized Evaluation of Midline Fascial Closure in Gastric Bariatric Operations," American Journal of Surgery, 172(4):328-31, October 1996

31 Anthony et al., "Factors Affecting Recurrence Following Incisional Herniorrhaphy," World Journal of Surgery, 2491):95-101, January 2000

32 Weller et al., "Comparing Outcomes of Laparoscopic Versus Open Bariatric Surgery," Annals of Surgery, 24891): 10-15, July 2008

33 Hedley et al., "Prevalence of overweight and obesity among US children, adolescents, and adults, 1999-2002," JAMA, 291:2847-2850, 2004

34 National Hospital Discharge Survey: Detailed Diagnoses and Procedures, CDC National Center for Health Statistics, 1995

25 Thorpe et al., "The impact of obesity on risking medical spending," Health Aff (Millwood), 2004, suppl. web exclusives: w4-480-w4-486

26 Franz, M. G., "The biology of hernia formation," Surg. Clin. North Am., 2008. 88(1): p. 1-15, vii.

27 Pollock et al., "Early prediction of late incisional hernias," British Journal of Surgery, 1989. 76: p. 953-954

28 Burger et al., "Incisional hernia: early complication of abdominal surgery," World J Surg., 2005 29(12): p. 1608-1613

29 Hoer et al, "Factors influencing the development of incisional hernia. A retrospective study of 2,983 laparotomy patients over a period of 10 years," Chirurg, 2002. 73(5): p. 474-80.

30 Sugerman et al., "Greater risk of incisional hernia with morbidly obese than steroid-dependent patients and low recurrence with prefascial polypropylene mesh," The American Journal of Surgery, 1996, 171(1): p. 80-84.

31 Riou et al., "Factors influencing wound dehiscence," Am J Surg., 1992. 163(3): p. 324-30

32 Regnard et al., "Ventral incisional hernias: incidence, date of recurrence, localization and risk factors," Ital J Surg Sci, 1988, 18(3): p. 259-65

33 Merkow et al., "Effect of body mass indes on short-term outcomes after colectomy for cancer," J Am Col Surg, 2009, 208: p. 53-61.

34 Grace et al., "Incidence of incisional hernia following dehiscence of the abdominal wound," Proc R Soc Med, 1973. 66(11): p. 1091

35 Keill et al., "Abdominal wound dehiscence," Arch Surg, 1973. 106(4): p. 573

36 Alexander et al., "The causes of abdominal wound disruption," Surg Gynecol Obstet, 1966. 122(6): p. 1223

37 Baggish et al., "Abdominal wound disruption," Obstet Gynecol, 1975. 46(5): p. 530

38 Pitkin et al., "Abdominal hysterectomy in obese women," Surg Gynecol Obstet, 1976. 142(4): p. 532

39 Bucknall, et al., "Burst abdomen and incisional hernia: a prospective study of 1129 major laparotomies," Br Med J (Clin Res Ed), 1982. 284(6320): p. 931-3.

40 Lamont et al., "Incisional hernia in re-opened abdominal incisions: an overlooked risk factor," Br J_Surg, 1988. 75(4): p. 374-6.

41 Kupczyk-Joeris et al., "Incisional hernia. Causes and principles of repair," Zentralbl Chir, 1990. 115(18): p. 1161-7
42 Hesselink et al., "An evaluation of risk factors in incisional hernia recurrence," Surg Gynecol Obstet, 1993. 176(3): p. 228-34
43 da Silva et al., "Incisional hernias: factors influencing development," South Med J, 1991. 84(12): p. 1500, 1504
44 Cleveland et al., "Incisional closure in morbidly obese patients," Am Surg, 1989. 55(1): p. 61-3
45 Luijendijk et al., "A comparison of suture repair with mesh repair for incisional hernia," New England Journal of Medicine, 2000. 343(6): p. 392-398
46 Carlson, M. A., "Acute wound failure," Surg Clin North Am, 1997. 77(3): p. 607-36
47 Burger et al., "Long-term follow-up of a randomized controlled trial of suture versus mesh repair of incisional hernia," Ann. Surg., 2004. 240(4): p. 578-583
48 Sauerland et al., "Obesity is a Risk Factor for Recurrence after Incisional Hernia Repair," Hernia, 2004. 8(1): p. 42-46
49 Nascimento et al., "Overweight induced by high-fat diet delays rat cutaneous wound healing," Br J Nut, 2006. 96(6): p. 1069-77
50 Goodson et al., "Wound collagen accumulation in obese hyperglycemic mice," Diabetes, 1986, 35(4): p. 491-5.
51 Biondo-Simoes Mde, L., et al., "Obesity and abdominal wound healing in rats," Acta Cir Bras. 25(1): p. 86-92
52 DuBay et al., "Progressive fascial wound failure impairs subsequent abdominal wall repairs: a new animal model of incisional hernia formation," Surgery, 2005. 137(4): p. 463-71
53 DuBay et al., "Incisional herniation induces decreased abdominal wall compliance via oblique muscle atrophy and fibrosis," Ann Surg, 2007. 245(1): p. 140-6
54 Franz et al., "Fascial incisions heal faster than skin: a new model of abdominal wall repair," Surgery, 2001, 129(2): P. 203-8
55 Franz et al., "Fascial incisions heal faster than skin: a new model of abdominal wall repair," Surgery, 2001, 129(2): p. 203-208
56 Dubay et al., "Progressive fascial wound failure impairs subsequent abdominal wall repairs: a new animal model of incisional hernia formation Surgery," 2005, 137(4): p. 463-471
57 Puchtler et al., "Polarization microscopic studies of connective tissue stained with picro-sirius red FBA," Beitr Pathol, 1973. 150(2): p. 17487
58 Junqueira et al, "Differential histologic diagnosis of osteoid A Study on human osteosarcoma collagen by the histochemical picrosirius-polarization method," J Pathol, 1986, 148(2) p. 189-96
59 Montes et al., "Histochemical and morphological characterization of reticular fibers," Histochemistry, 1980, 65(2): p. 131-41
60 Pollock et al., "Early prediction of late incisional hernias," Br J Surg, 1989. 76(9): p. 953.4
61 Dubay et al., "Fascial fibroblast kinetic activity is increased during abdominal wall repair compared to dermal fibroblasts," Wound Repair Regen, 2004. 12(5): p. 539-45
62 Baum et al., "Normal cutaneous wound healing: clinical correlation with cellular and molecular events," Dermatol Surg, 2005. 31(6): p. 674-86; discussion 686
63 Goodson et al., "Deficient collagen formation by obese mice in a standard wound model.," Am J Surg, 1979. 138 (5): p. 692-4
64 Vrabec, J. T., "Tympanic membrane perforations in the diabetic rat: a model of impaired wound healing," Otolaryngol Head Neck Surg, 1998. 118 (3 Pt 1): p. 304-8
65 Kurtz et al., "The Zucker fatty rat as a genetic model of obesity and hypertension," Hypertension, 1989. 13(6 Pt 2): p. 896-901
66 Bray, G A., "The Zucker-fatty rat: a review," Fed Proc, 1977, 36(2): p. 148-53
67 Metz et al., "Fibrocytes: a unique cell population implicated in wound healing," Cell Mol Life Sci, 2003. 60(7): p. 1342-50

The invention claimed is:

1. A method of decreasing incisional hernia formation in a patient comprising administering to the patient a therapeutically effective amount of a composition comprising basic fibroblast growth factor,
wherein the composition is administered during a surgical procedure performed or to be performed on the patient,
wherein the patient is obese,
wherein the patient has impaired fibroblast function, and
wherein the surgical procedure is a bariatric surgery.

2. The method of claim 1, wherein an incision is made to fascia of a musculofascial layer of the abdominal wall of the patient.

3. The method of claim 2, wherein the composition is administered at about the time of the incision.

4. The method of claim 3, wherein the composition is administered into the fascia.

5. The method of claim 2, wherein the composition is administered at about the time of closure of the fascia.

6. The method of claim 5, wherein the composition is administered into the fascia.

7. The method of claim 5, wherein the composition is administered into one or more edges of the fascia.

8. The method of claim 5, wherein the composition is administered into the musculofascial layer.

9. The method of claim 8, wherein the composition is administered into one or more edges of the musculofascial layer.

10. The method of claim 2, wherein the composition is administered at about the time of the incision to the fascia and at about the time of closure of the fascia.

11. The method of claim 10, wherein the composition is administered into the fascia, the musculofascial layer, or both.

12. The method of claim 2, wherein the basic fibroblast growth factor is present in an amount between about 0.1 microgram and about 10 micrograms per centimeter of the incision.

13. The method of claim 2, wherein the basic fibroblast growth factor is present in an amount between about 1 microgram and about 5 micrograms per centimeter of the incision.

14. The method of claim 2, wherein the basic fibroblast growth factor is present in an amount of about 5 micrograms per centimeter of the incision.

15. The method of claim 2, wherein the basic fibroblast growth factor is present in an amount of about 3 micrograms per centimeter of the incision.

16. The method of claim 2, wherein the basic fibroblast growth factor is present in an amount of about 1 microgram per centimeter of the incision.

17. The method of claim 1, wherein the composition is administered as a single dose during the surgical procedure performed or to be performed on the patient.

18. The method of claim 1, wherein the composition is administered as a single unit dose during the surgical procedure performed or to be performed on the patient.

19. The method of claim 1, wherein the composition further comprises a carboxymethylcellulose vehicle.

20. The method of claim 1, wherein the composition further comprises a hyaluronic acid vehicle.

21. The method of claim 1, wherein the composition further comprises a fibrin glue vehicle.

22. The method of claim 1, wherein the patient has a body mass index greater than 35.

23. A method of decreasing acute wound failure in a patient comprising administering to the patient a therapeutically effective amount of a composition comprising basic fibroblast growth factor,
wherein the patient is obese,
wherein the patient has impaired fibroblast function, and
wherein the composition is administered during a bariatric surgical procedure performed or to be performed on the patient.

24. The method of claim 23, wherein an incision is made to fascia of a musculofascial layer of the abdominal wall of the patient.

25. The method of claim 24, wherein the composition is administered at about the time of the incision.

26. The method of claim 25, wherein the composition is administered into the fascia.

27. The method of claim 24, wherein the composition is administered at about the time of closure of the fascia.

28. The method of claim 27, wherein the composition is administered into the fascia.

29. The method of claim 27, wherein the composition is administered into one or more edges of the fascia.

30. The method of claim 27, wherein the composition is administered into the musculofascial layer.

31. The method of claim 27, wherein the composition is administered into one or more edges of the musculofascial layer.

32. The method of claim 24, wherein the composition is administered at about the time of the incision and at about the time of closure of the fascia.

33. The method of claim 32, wherein the composition is administered into the fascia, the musculofascial layer, or both.

34. The method of claim 24, wherein the basic fibroblast growth factor is present in an amount between about 0.1 microgram and about 10 micrograms per centimeter of the incision.

35. The method of claim 28, wherein the basic fibroblast growth factor is present in an amount between about 1 microgram and about 5 micrograms per centimeter of the incision.

36. The method of claim 24, wherein the basic fibroblast growth factor is present in an amount of about 5 micrograms per centimeter of the incision.

37. The method of claim 24, wherein the basic fibroblast growth factor is present in an amount of about 3 micrograms per centimeter of the incision.

38. The method of claim 24, wherein the basic fibroblast growth factor is present in an amount of about 1 microgram per centimeter of the incision.

39. The method of claim 23, wherein the composition is administered as a single dose during the surgical procedure performed or to be performed on the patient.

40. The method of claim 23, wherein the composition is administered as a single unit dose during the surgical procedure performed or to be performed on the patient.

41. The method of claim 23, wherein the composition further comprises a carboxymethylcellulose vehicle.

42. The method of claim 23, wherein the composition further comprises a hyaluronic acid vehicle.

43. The method of claim 23, wherein the composition further comprises a fibrin glue vehicle.

44. The method of claim 23, wherein the patient has a body mass index greater than 35.

45. A method of decreasing acute wound failure of an abdominal wall comprising administering to fascia of a musculofascial layer of the abdominal wall a therapeutically effective amount of a composition comprising basic fibroblast growth factor, wherein the incision is made on an obese patient during a bariatric surgical procedure, and wherein the patient has impaired fibroblast function.

46. The method of claim 45, wherein the composition is administered to a location where an incision is to be made in the fascia.

47. The method of claim 46, wherein the administration is about the time of making the incision.

48. The method of claim 47, wherein the composition is administered into the fascia.

49. The method of claim 45, wherein the composition is administered to an incision in the fascia upon closure of the fascia.

50. The method of claim 49, wherein the composition is administered into the fascia.

51. The method of claim 49, wherein the administration is to one or more edges of the fascia.

52. The method of claim 46, wherein the composition is administered at about the time of the incision to the fascia and at about the time of closure of the fascia.

53. The method of claim 52, wherein the composition is administered into the fascia, the musculofascial layer, or both.

54. The method of claim 46, wherein the basic fibroblast growth factor is present in an amount between about 0.1 microgram and about 10 micrograms per centimeter of the incision.

55. The method of claim 46, wherein the basic fibroblast growth factor is present in an amount between about 1 microgram and about 5 micrograms per centimeter of the incision.

56. The method of claim 46, wherein the basic fibroblast growth factor is present in an amount of about 5 micrograms per centimeter of the incision.

57. The method of claim 46, wherein the basic fibroblast growth factor is present in an amount of about 3 micrograms per centimeter of the incision.

58. The method of claim 46, wherein the basic fibroblast growth factor is present in an amount of about 1 microgram per centimeter of the incision.

59. The method of claim 46, wherein the composition is administered as a single dose.

60. The method of claim 46, wherein the composition is administered as a single unit dose.

61. The method of claim 46, wherein the composition further comprises a carboxymethylcellulose vehicle.

62. The method of claim 46, wherein the composition further comprises a hyaluronic acid vehicle.

63. The method of claim 46, wherein the composition further comprises a fibrin glue vehicle.

64. The method of claim 46, wherein the patient has a body mass index greater than 35.

* * * * *